United States Patent
Helmore et al.

(10) Patent No.: US 7,566,885 B2
(45) Date of Patent: Jul. 28, 2009

(54) DEVICE FOR STERILIZING A FLUID

(76) Inventors: Ian Stewart Helmore, 24 The Sycamores, Baldock, Hertfordshire SG7 5BJ (GB); Stephen Neville Croft, 27 Ashwell Close, Graveley, Hitchin, Hertfordshire SG7 7LH (GB)

( * ) Notice: Subject to any disclaimer, the term of this patent is extended or adjusted under 35 U.S.C. 154(b) by 386 days.

(21) Appl. No.: 10/546,488

(22) PCT Filed: Feb. 20, 2004

(86) PCT No.: PCT/GB2004/000672

§ 371 (c)(1),
(2), (4) Date: Apr. 11, 2006

(87) PCT Pub. No.: WO2004/073754

PCT Pub. Date: Sep. 2, 2004

(65) Prior Publication Data

US 2006/0192137 A1 Aug. 31, 2006

(30) Foreign Application Priority Data

Feb. 22, 2003 (GB) .................................. 0304070.6

(51) Int. Cl.
*C02F 1/30* (2006.01)
*C02F 1/32* (2006.01)
(52) U.S. Cl. ............................ 250/455.11; 250/453.11; 250/454.11; 210/739; 210/744
(58) Field of Classification Search ............ 250/453.11, 250/454.11, 455.11
See application file for complete search history.

(56) References Cited

U.S. PATENT DOCUMENTS 3,250,294 A * 5/1966 Hipple ...................... 137/528
4,102,645 A * 7/1978 Meacham et al. ....... 250/432 R
4,672,613 A 6/1987 Foxworthy et al.
5,288,412 A * 2/1994 Voorhees et al. ............ 210/739
5,393,419 A 2/1995 Tiede et al.
5,891,329 A 4/1999 Massholder
6,486,419 B2 10/2002 Kunkel
6,497,840 B1 12/2002 Palestro et al.

FOREIGN PATENT DOCUMENTS

| | | |
|---|---|---|
| DE | 19639802 | 4/1998 |
| DE | 20105341 | 8/2002 |
| DE | 10157355 | 6/2006 |
| JP | 59-136188 | 8/1984 |

(Continued)

*Primary Examiner*—David A. Vanore
(74) *Attorney, Agent, or Firm*—Haugen Law Firm PLLP (57) ABSTRACT

A device (2) for sterilizing a fluid comprising a sterilization zone (4) having an outlet portion (10), comprising at least one aperture (16) through which the fluid may exit the device (2), wherein the sterilization zone (4) is arranged to be irradiated by a source of ultraviolet radiation (18) such that substantially all of the internal surfaces of the outlet portion (10) are directly irradiated by the source of ultraviolet radiation (18) and wherein the source of ultraviolet radiation (18) and the at least one aperture (16) are arranged such that substantially no ultraviolet radiation may be transmitted directly from the source of ultraviolet radiation (18) through the at least one aperture (16). Preferably the device (2) comprises a shower unit. There is also disclosed a method of sterilizing a fluid.

17 Claims, 5 Drawing Sheets

FOREIGN PATENT DOCUMENTS

| | | |
|---|---|---|
| JP | 59136188 | 8/1984 |
| JP | 3 177710 | 8/1991 |
| JP | 8-66677 | 3/1996 |
| JP | 91 73233 | 7/1997 |
| JP | 10 296246 | 11/1998 |
| JP | 2000 084545 | 3/2000 |
| JP | 2000 201569 | 7/2000 |
| JP | 2001 334179 | 12/2001 |
| JP | 2002 517002 | 6/2002 |
| JP | 2002 301379 | 10/2002 |
| WO | WO 97/30938 | 8/1997 |
| WO | WO 00/78366 | 12/2000 |

* cited by examiner

DEVICE FOR STERILIZING A FLUID

The present invention relates to a device for sterilising a fluid, in particular to a device for sterilising a fluid using ultraviolet radiation.

It is well known that bacteria and other micro-organisms can be killed by the use of electromagnetic radiation such as ultraviolet radiation. In particular, ultraviolet radiation may be used to sterilise a source of water by passing the water near to a source of ultraviolet radiation for a sufficient time for any micro-organisms to be killed. It is also known to use this process in a batch or a continuous manner.

One particular use of such water sterilisation devices is to sterilise the water for use in a shower. Because of their nature, showers can produce a fine mist which may be inhaled by the user of the shower. If the water is infected with the legionella bacteria this can have potentially fatal results. Some prior art devices contain ultraviolet sources which are periodically turned off if no water is flowing. If the water begins to flow before the ultraviolet source reaches optimum performance, there is a danger of micro-organisms flowing past the ultraviolet source without being killed.

To address this problem, some prior art devices have a delaying mechanism whereby flow of water is delayed until the ultraviolet source reaches optimum performance. However, this may lead to a user, unaware of this delaying mechanism, thinking that the water supply is faulty and leaving the shower or tap left open. This may lead to unwanted flooding.

Other prior art systems use ultraviolet radiation to sterilise a fluid some distance upstream of the point of exit of the fluid from the system. If the fluid is flowing slowly, or periodically stops flowing, there is the danger of harmful microorganisms being introduced into the fluid downstream of the ultraviolet radiation source. These systems cannot provide a sterilised source of fluid under these conditions.

It is therefore apparent that there exists a need for an improved device for sterilising a fluid.

According to one aspect of the present invention there is provided a device for sterilising a fluid comprising a sterilisation zone having an outlet portion comprising at least one aperture through which the fluid may exit the device, wherein the sterilisation zone is arranged to be irradiated by a source of ultraviolet radiation such that substantially all of the internal surfaces of the outlet portion are directly irradiated by the source of ultraviolet radiation and wherein the source of ultraviolet radiation and the at least one aperture are arranged such that substantially no ultraviolet radiation may be transmitted directly from the source of ultraviolet radiation through the at least one aperture.

Preferably, the outlet portion defines an elongate volume extending away from the source of ultraviolet radiation.

Conveniently, the at least one aperture leads to an open air space.

Advantageously, the outlet portion extends continuously to the source of ultraviolet radiation.

Preferably, the outlet portion comprises a shower head.

Conveniently, the device further comprises a casing which prevents removal of the shower head.

Advantageously, the outlet portion comprises a tap.

Preferably, the device comprises stainless steel.

Conveniently, the source of ultraviolet radiation is an ultraviolet lamp.

Advantageously, the source of ultraviolet radiation is contained within a quartz housing.

Preferably, the device has a substantially tubular configuration with the source of ultraviolet radiation positioned substantially along the longitudinal axis of the device.

Conveniently, the device is positioned in use with the outlet portion projecting at least partly upwardly from the remainder of the device.

Advantageously, the device is arranged such that the source of ultraviolet radiation is shut off if the device is opened.

Preferably, the device comprises means to shut off the flow of fluid if the source of ultraviolet radiation is off.

Conveniently, the means to shut off the flow of fluid comprises a pulse latching valve.

Advantageously, the means to shut off the flow of fluid is powered by a capacitor.

Preferably, the device further comprises means to prevent flow of fluid through the device for a predetermined period of time after the source of ultraviolet radiation is activated.

Embodiments of the present invention will now be described, by way of example, with reference to the accompanying drawings in which.

Figure 1:
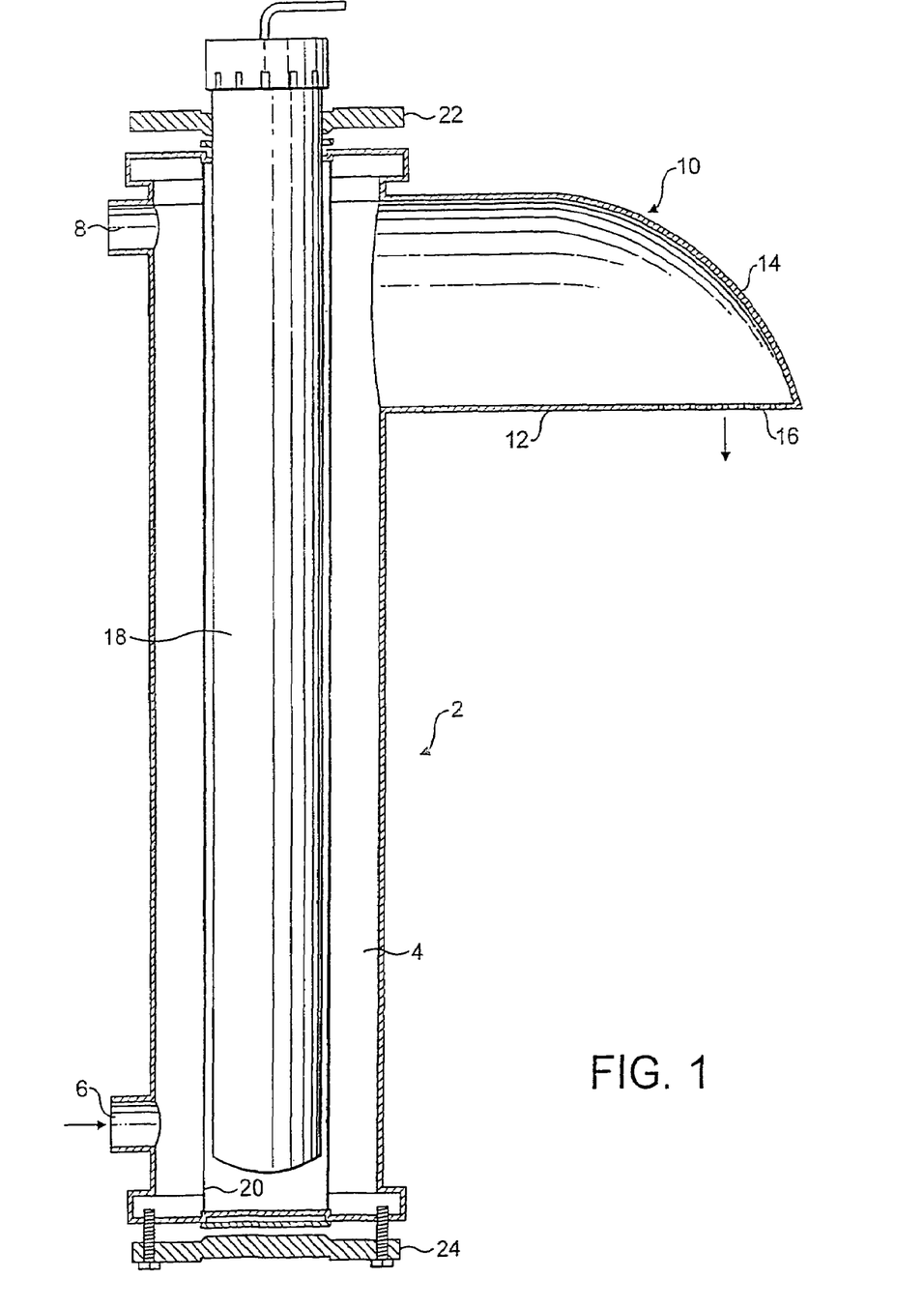
FIG. 1 is a cross-section of a device according to the present invention.

Turning to FIG. 1, a device according to the invention is shown generally at 2, having a substantially tubular configuration. Although the device 2 is described herein with reference to a unit to provide sterile water for a shower, it is to be appreciated that other embodiments are possible. For example, the devices of the invention are applicable to a wide range of fluids, including gases and liquids other than water. Also, although a shower unit is described, the invention is also applicable to fluid outlets such as basin or bath taps. Thus the present invention has a wide range of applications such as use in medical, consumer and food related environments such as hotels and hospitals.

The device 2 comprises an elongate chamber 4 bounded by a substantially cylindrical wall. In use, the device 2 is positioned in a substantially vertical configuration, as explained below.

Towards the lower end of the chamber 4 there is located an inlet 6 for the passage of water into the chamber 4. Towards the top end of the chamber 4 there is located an opening 8, the purpose of which will be described below. Towards the top end of the chamber 4 there is also located an outlet 10 having a substantially tubular configuration which projects and tapers away from the chamber 4. The outlet 10 has a lower wall 12 which extends in a substantially straight line away from the chamber 4. The outlet 10 has an upper wall 14 which curves down to meet the lower wall 12. A region of the lower wall 12 is provided with a number of apertures 16, thus forming a shower rose.

A tubular ultraviolet (UV) lamp 18 is located substantially centrally along the longitudinal axis of the chamber 4. The UV lamp 18 is located within a concentric cylindrical quartz sleeve 20. Liquid-tight fittings 22 and 24 are located at the ends of the chamber 4 to locate the quartz sleeve 20 and the UV lamp 18 within the chamber 4 in a liquid-tight manner.

As mentioned above, there is an outlet 8 positioned towards the upper end of chamber 4. Outlet 8 leads to a sensor which detects whether the UV lamp 18 is turned on or off.

Water may enter the device 2 through inlet 6 and pass into the annular space in chamber 4 around the quartz sleeve 20. The water flows up and around the quartz sleeve 20, being irradiated by the UV lamp 18. The water then flows through the outlet 10 and passes out of the device 2 through the apertures 16. The device 2 thus provides a spray of water in a similar way to a traditional shower.

Whilst water is flowing, the device 2 is arranged such that any micro-organisms present in the water are irradiated with enough ultraviolet radiation in order to kill them. The device 2 shown has a UV lamp 18 with a power of 15 W and could safely sterilise a flow of water of up to 8 liters/minute. In use, the device 2 typically provides a maximum flow of around 6 liters/minute. If the sensor located at outlet 8 detects that the UV lamp 18 is turned off, it activates a valve which shuts off the water supply to inlet 6. Thus, the passage of water through the device 2 whilst the ultraviolet lamp 18 is turned off is prevented ensuring that only sterile water leaves the apertures 16.

There are also means for detecting the opening of the chamber 4, for example by unscrewing the outlet 10 from the wall of the chamber 4. If it is detected that the clamber 4 is opened, the valve again shuts off the water supply to the device 2 to prevent any unwanted exposure to the UV radiation.

The outlet 10 is shaped and located relative to the UV lamp 18 such that substantially all of the inner surfaces of outlet 10 are directly irradiated by the UV lamp 18. Thus, the device 2 ensures that both the water and the surfaces over which it flows right up until the point of exit of the device 2 are irradiated and thus sterile.

It is to be appreciated that other configurations of the device are possible-which still achieve the same result. The important feature is for the device to be arranged such that substantially all of the internal surfaces of the outlet portion of the device are irradiated by the ultraviolet source, right up to the point of exit of the fluid from the device.

Also, the UV lamp 18 is normally left switched on in order to maintain a sterile environment within the chamber 4 of the outlet 10. Thus, a user may shut off the water flowing through the device 2 whilst not in use, with UV lamp 18 remaining turned on. This has the advantage of prolonging the life of the UV lamp, which is degraded by intermittent use. Also, the constant irradiation of the inner surfaces of the device 2 whilst the water is not flowing prevents contamination by killing any microorganisms which may enter the device. Furthermore, because the UV lamp 18 is already on and at optimum performance, there is no need to delay the flow of water. Thus the disadvantages of such a delay are avoided.

It is to be appreciated however that an alternative embodiment may be provided in which the lamp 18 is activated only when there is a flow of water. This embodiment would benefit from the complete sterilisation of the inner surfaces of the device up to the point of exit of the water.

As ultraviolet light may be harmful to the user of the device 2, the outlet 10 is arranged such that substantially no UV radiation is directly transmitted from the UV lamp 18 through the apertures 16 to leave the device 2. In other words, it is not possible to directly view the UV lamp 18 through the apertures 16.

When there is no flow of water, the device 2 is maintained full of water. The apertures 16 and the outlet 10 are arranged to minimise egress of water through the aperture 16 under these conditions.

Figure 2:
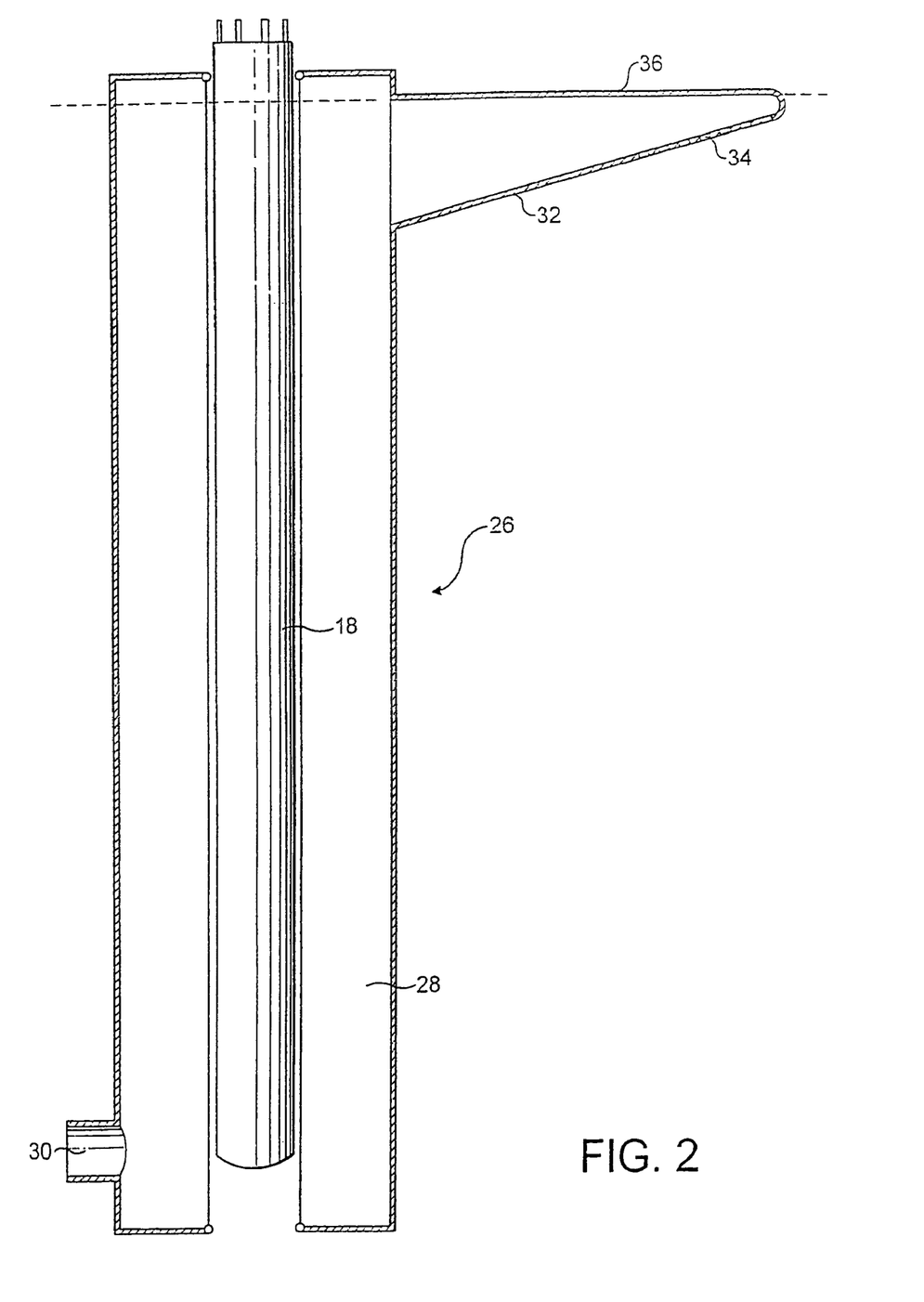
FIG. 2 is a cross-section of an alternative embodiment of a device according to the invention.

FIG. 2 shows an alternative embodiment of the invention. Device 26 comprises a tubular chamber 28 having an inlet 30 and an outlet 32. In this embodiment the outlet 32 projects outwardly and upwardly from the annular chamber 28. Apertures 34 are located on the lower surface of outlet 32 towards the end thereof. This has the advantage of minimising the pressure of the water located within the outlet 32 in the vicinity of the apertures 34 whilst water is not flowing through the device 26. Thus the chances of liquid being lost through the apertures 34 whilst liquid is not flowing through the device are reduced. The embodiment shown has an outlet 32 with a substantially horizontal upper wall 36. As indicated, the upper wall 36 is positioned slightly below the highest point of the chamber 28. This results in a small head of pressure in the outlet 32 ensuring that the outlet remains full of water. In alternative embodiments, the outlet could project higher than the highest point of the chamber.

Figure 3:
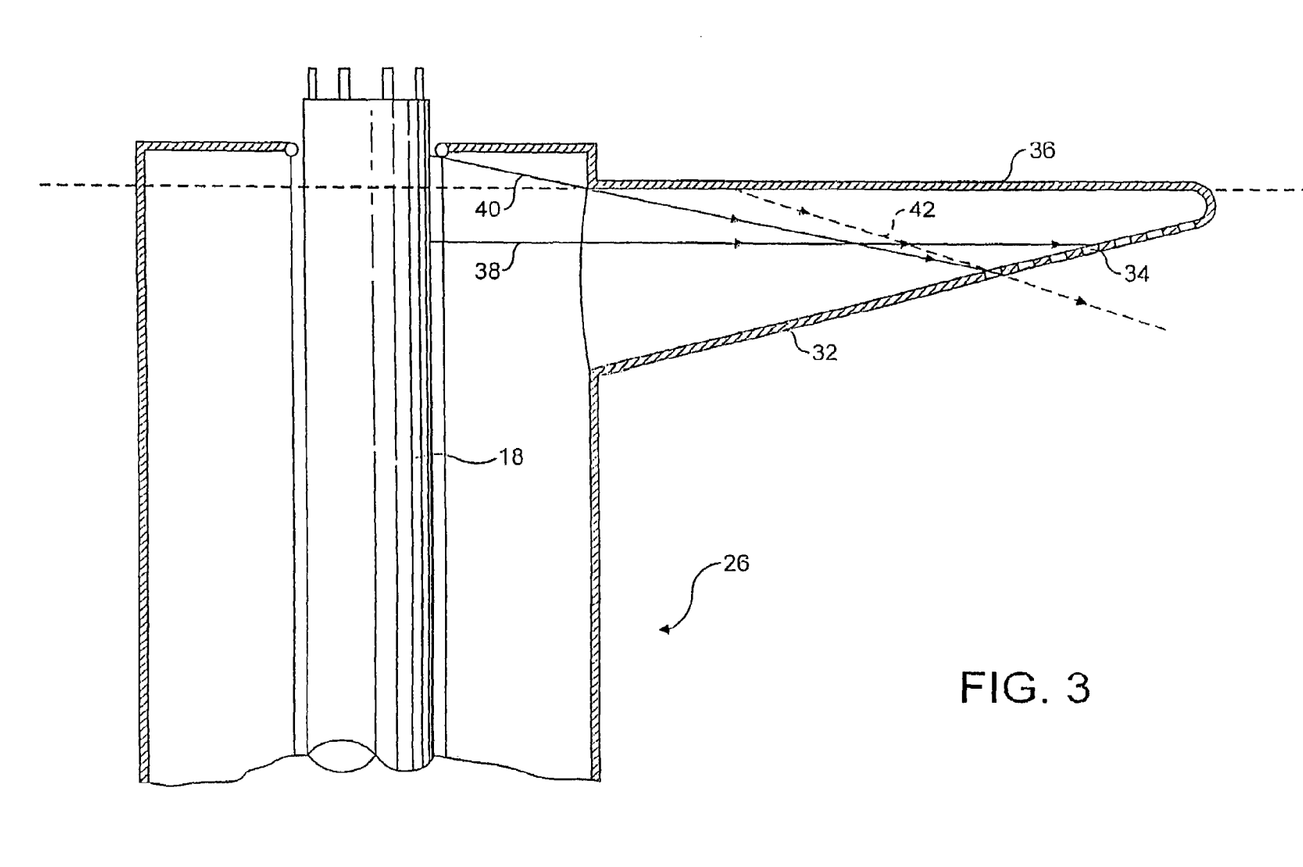
FIG. 3 is a partial cross-section of the outlet of a device of the invention.

FIG. 3 is a large-scale view of the top portion of the device 26 shown in FIG. 2. As discussed, above, the lamp 18 directly illuminates substantially all of the internal surfaces of the outlet 32, without UV radiation escaping directly through the apertures 34. In the embodiment shown, this result is achieved simply by the size and position of the apertures 34 relative to the lamp 18 and the thickness of the wall of the outlet 32.

Line 38 illustrates the path of UV radiation from a point on the lamp 38 substantially horizontally into the outlet 32. As shown, although the path 38 enters an aperture 34, it terminates on the inner wall of that aperture distal to the lamp 18. Thus UV radiation along path 38 cannot directly pass out of the device 26 through the apertures 34.

Line 40 illustrates the path from the highest possible point of lamp 40 to the apertures 34. Even though the path 40 is angled more steeply into the apertures 34 than path 38, the path 40 still terminates on the inner surface of an aperture. Thus light from the lamp 18 travelling on path 40 cannot directly escape through the apertures 34.

Path 42 shows the minimum angle needed for light to directly pass through the apertures 34. It can be seen that a user of the device cannot see through the apertures 34 to see the lamp 18.

Although the invention has been described with reference to outlets having an integral shower rose, it is to be appreciated that outlets with detachable or removable shower roses are also possible. In such cases, the device is preferably arranged so that there is no direct optical path to the lamp from outside the device even if the shower rose is removed.

Also, as mentioned above, the invention is applicable to fluid outlets in general, including basin taps. In some circumstances, a sterilisation unit for a basin may be arranged with an outlet towards the bottom of the device. Whilst water (or other fluids) are not flowing through such a device, there would exist a larger pressure at the outlet than with the arrangements shown in the accompanying figures. Whilst the device is preferably arranged to retain a full body of water in such circumstances, further means for preventing water loss may be required. Such means may, for example, reduce the pressure inside the device using techniques apparent to those skilled in the art. It is preferable to avoid moving parts in order to minimise manufacture and services costs and to avoid possible non-sterile portions within such a device.

Figure 4:
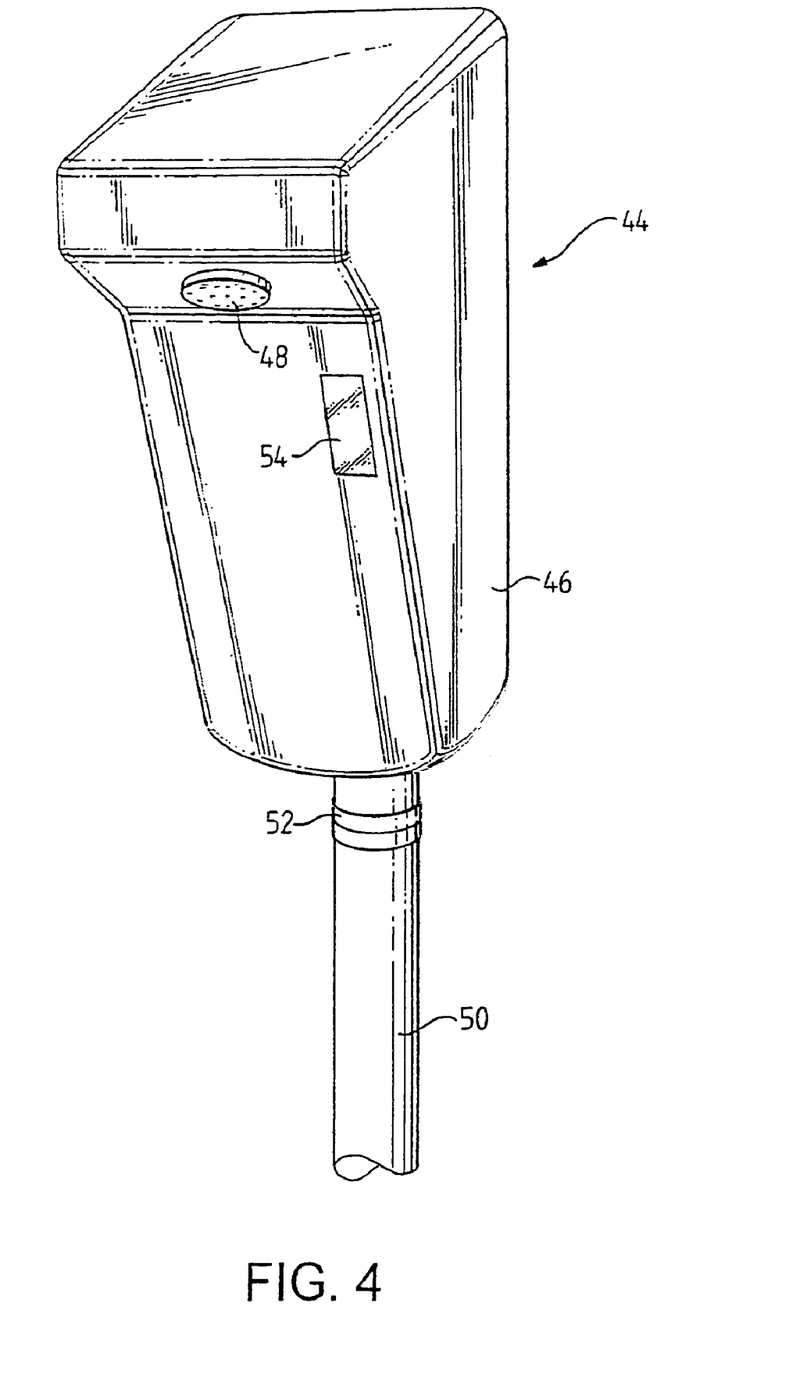
FIG. 4 is a perspective view of a further embodiment of the invention.

FIG. 4 shows a further embodiment of the invention comprising a wall-mounted shower unit 44. The unit 44 has a plastic casing 46 through which protrudes a shower rose 48. A flexible water inlet hose 50 is connected to the base of the unit 44 using a snap fit connector 52. On the front face of the casing 46 there is a clear window 54.

Figure 5:
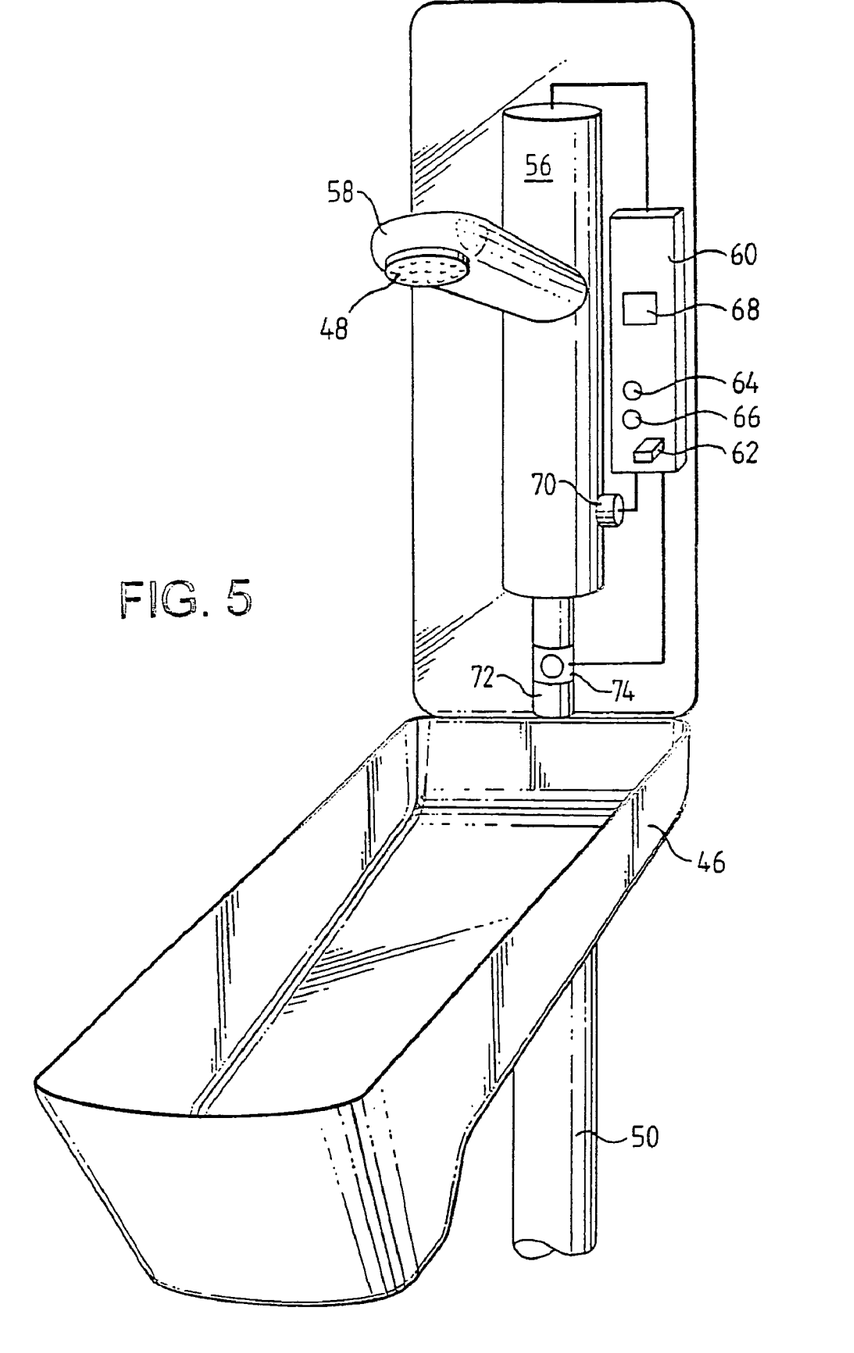
FIG. 5 is a perspective view of the embodiment shown in FIG. 4 with its casing in an open position.

FIG. 5 shows the unit 44 with the front casing 46 hinged open. The components of the device 44 comprise a sterilisation tube 56 containing a UV lamp. The tube 56 has an outlet portion 58 projecting therefrom which terminates in the shower rose 48. The casing 46 has an aperture through which the shower rose 48 projects when the casing 46 is in a closed position. The shower rose 48 is attached to the outlet portion 58 in such a way as to prevent the removal of the rose 48 whilst the casing 46 is closed. The casing 46 must be opened before the rose 48 can be removed. As will be described below, this prevents the accidental exposure of a user to UV radiation by the unit. A control unit 60 comprises electronic components which control the functioning of the unit. On the control unit 60 there is provided a sensor 62 which detects whether the casing 46 is opened or closed. When the casing 46 is opened, the sensor 62 is activated and the UV lamp is automatically switched off.

There is a water inlet pipe 72 leading from the connector 52 to the base of the sterilisation tube 56. The inlet pipe 72 is provided with a shut-off valve 74 which is controlled by the control unit 60. When the switch 62 is activated by the opening of the casing 46, the control unit 60 activates the valve 74 to shut off the flow of liquid through the device. This prevents potentially unsterilised liquid from leaving the device 44. Preferably, the valve 74 is a pulse latching valve which operates via a magnetic pulse. The valve 74 is activated by a capacitor. Thus, in the event of power failure, the capacitor powers the valve 74, allowing it to close, again preventing the flow of potentially unsterilised water through unit 44.

When the casing 46 is opened without the electrical power to the device being turned off, the warning light 68 is activated to warn the user of this fact.

When the device is initially switched on, the red indicator light 64 is activated to indicated that the unit is powered but not yet operational. The control unit 60 activates the UV lamp in the sterilisation tube 56 but prevents water from flowing through the unit for a predetermined period of two minutes. Depending on the circumstances, other periods of time could be used. This delay is provided to allow the UV lamp to reach optimum working conditions and to give sufficient time for the sterilisation of the water already contained within the unit. Once the predetermined period of time ends, the red light 64 is turned off and the green light 66 is turned on to show that normal operating conditions have been reached. The control unit 60 then opens the valve 74, allowing water to flow through the device.

There is also provided a photosensor 70 which detects the emission of UV radiation from the UV lamp within the sterilisation tube 56. If the lamp fails or if the level of radiation has dropped below a predetermined safe minimum value, the control unit 60 closes the valve 74 and turns off the UV lamp. The red light 64 is then turned on in a flashing mode to alert the user of the situation. The UV lamp can then be replaced or repaired in order for the unit to become operational again.

Under certain circumstances, a user may wish to rinse a fitting such as a bath. In order to do so, the flexible hose 50 may be disconnected via the connector 52 from the unit 44 and used to rinse such a fitting. As micro-organisms such as legionella are normally only harmful when present in a mist or aerosol of water droplets, the use of a water hose in this way should not pose any risk.

It is to be appreciated that the water inlet for the unit 44 could be provided at the back of the device. Thus, the user would be presented with only the unit 44 mounted on a wall without any visible external water connections.

Other embodiments are possible where the bulk of the unit is located within a cavity behind a wall or other such configurations such that only the water outlet or shower rose is visible. Also, the device, or parts thereof, may be constructed from materials other than stainless steel, including metals such as copper and plastics such as ABS, nylon and u-PVC.

What is claimed is:

1. A device for sterilizing a fluid comprising a sterilization zone having an outlet portion comprising at least one aperture through which the fluid may exit the device, wherein the sterilization zone is affanged to be irradiated by a source of ultraviolet radiation such that substantially all internal surfaces of the sterilization zone are in direct optical communication with the source of ultraviolet radiation so as to be directly irradiated by the source of ultraviolet radiation and wherein the source of ultraviolet radiation and the at least one aperture are arranged such that substantially no ultraviolet radiation may be transmitted directly from the source of ultraviolet radiation through the at least one aperture.

2. A device according to claim 1 wherein the outlet portion defines an elongate volume extending away from the source of ultraviolet radiation.

3. A device according to claim 1 wherein the at least one aperture leads to an open air space.

4. A device according to claim 1, wherein the outlet portion extends continuously to the source of ultraviolet radiation.

5. A device according to claim 1 wherein the outlet portion comprises a shower head.

6. A device according to claim 5 wherein the device further comprises a casing which prevents removal of the shower head.

7. A device according to claim 1 wherein the outlet portion comprises a tap.

8. A device according to claim 1 comprising stainless steel.

9. A device according to claim 1 wherein the source of ultraviolet radiation is an ultraviolet lamp.

10. A device according to claim 1 wherein the source of ultraviolet radiation is contained within a quartz housing.

11. A device according to claim 1 having a substantially tubular configuration with the source of ultraviolet radiation positioned substantially along the longitudinal axis of the device.

12. A device according to claim 1 which is positioned in use with the outlet portion projecting at least partly upwardly from the remainder of the device.

13. A device according to claim 1 which is arranged such that the source of ultraviolet radiation is shut off if the device is opened.

14. A device according to claim 1 wherein the device comprises means to shut off the flow of fluid if the source of ultraviolet radiation is off.

15. A device according to claim 14 wherein the means to shut off the flow of fluid comprises a pulse latching valve.

16. A device according to claim 14 wherein the wherein the means to shut off the flow of fluid is powered by a capacitor.

17. A device according to claim 1 further comprising means to prevent flow of fluid through the device for a predetermined period of time after the source of ultraviolet radiation is activated.

* * * * *

UNITED STATES PATENT AND TRADEMARK OFFICE
CERTIFICATE OF CORRECTION

PATENT NO. : 7,566,885 B2
APPLICATION NO. : 10/546488
DATED : July 28, 2009
INVENTOR(S) : Ian Stewart Helmore et al.

Page 1 of 1

It is certified that error appears in the above-identified patent and that said Letters Patent is hereby corrected as shown below:

Column 3, line 30, replace "possible-which" with -- possible which --.

Column 6, line 9, replace "affanged" with -- arranged --.

Claim 16, column 6, line 53, replace "wherein the wherein the" with -- wherein the --.

Signed and Sealed this

Eighth Day of September, 2009

David J. Kappos
*Director of the United States Patent and Trademark Office*